United States Patent
Ahmed et al.

(10) Patent No.: US 10,799,724 B2
(45) Date of Patent: Oct. 13, 2020

(54) ORAL CARE COMPOSITIONS

(71) Applicant: Colgate-Palmolive Company, New York, NY (US)

(72) Inventors: Rabab Ahmed, Somerset, NJ (US); Michael Prencipe, West Windsor, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 15/768,918

(22) PCT Filed: Oct. 22, 2015

(86) PCT No.: PCT/US2015/056818
§ 371 (c)(1),
(2) Date: Apr. 17, 2018

(87) PCT Pub. No.: WO2017/069757
PCT Pub. Date: Apr. 27, 2017

(65) Prior Publication Data
US 2019/0076677 A1    Mar. 14, 2019

(51) Int. Cl.
*A61K 8/81*   (2006.01)
*A61Q 11/00*  (2006.01)
*A61K 31/167* (2006.01)
*A61K 31/245* (2006.01)

(52) U.S. Cl.
CPC ............ *A61Q 11/00* (2013.01); *A61K 8/8164* (2013.01); *A61K 31/167* (2013.01); *A61K 31/245* (2013.01)

(58) Field of Classification Search
CPC .......... A61K 2300/00; A61K 2039/505; A61K 45/06; A61K 47/6803; A61K 31/337; A61K 9/0019; A61K 39/3955; A61K 47/6849; A61K 31/135; A61K 31/437; A61K 38/00; A61K 31/424
See application file for complete search history.

(56) References Cited

U.S. PATENT DOCUMENTS

| | | |
|---|---|---|
| 4,118,480 A | 10/1978 | Williams |
| 4,241,048 A | 12/1980 | Durbak et al. |
| 5,362,737 A | 11/1994 | Vora et al. |
| 5,446,063 A | 8/1995 | Reuter et al. |
| 5,462,749 A | 10/1995 | Rencher |
| 5,714,165 A | 2/1998 | Repka et al. |
| 6,294,594 B1 | 9/2001 | Borja et al. |
| 6,375,963 B1 | 4/2002 | Repka et al. |
| 6,423,762 B1 * | 7/2002 | Wong .................. C08F 8/44 523/120 |
| 2009/0238776 A1 | 9/2009 | Baig et al. |

FOREIGN PATENT DOCUMENTS

| | | |
|---|---|---|
| CN | 101797209 | 8/2010 |
| DE | 29924651 | 9/2004 |
| RU | 2281083 | 6/2005 |
| WO | 1996/013244 | 5/1996 |
| WO | 2001/041711 | 6/2001 |
| WO | 2009/149030 | 12/2009 |
| WO | 2011/031807 | 3/2011 |
| WO | 2014/071203 | 5/2014 |

OTHER PUBLICATIONS

International Search Report and Written Opinion of the International Searching Authority in International Application No. PCT/US2015/056818, dated Jun. 15, 2016.
Morrison et al., 1996, "The scope of mineral oil in personal care products and its role in cosmetic formulations," J. Applied Cosmetology 14(3):111-118.
VIDAL Belarus Medicinal Product Directory, "Menovazan-Vishfa Instruction Manual" <https://www.vidal.by/poisk-preparatov/menovazan-vishfa.html>.
VIDAL Belarus Medicinal Product Directory, "Menovazan-Vishfa Instruction Manual" <https://www.vidal.by/poisk-preparatov/menovazan-vishfa.html> English language machine translation.

* cited by examiner

*Primary Examiner* — Nannette Holloman

(57) ABSTRACT

An oral care composition comprising a local anaesthetic agent, a film-forming polymer and a non-aqueous vehicle wherein the film-forming polymer comprises an alkyl vinyl ether-maleic acid or anhydride copolymer or salt thereof is provided.

13 Claims, No Drawings

ORAL CARE COMPOSITIONS

BACKGROUND

The present invention relates to oral care compositions comprising local anaesthetic and to methods using such compositions.

Aphthous ulcers (also commonly called mouth ulcers or canker sores) are characterized by the formation of painful lesions in the mucous membranes of the oral cavity. Generally, such ulcers are treated using topical local anaesthetic agents. Compositions for use in the oral cavity must be carefully formulated in order to provide effective relief in the oral cavity environment. In particular, the composition should be well retained on the surfaces of the oral cavity in order to be able to exert an anaesthetic effect. It would be desirable to provide improved formulations suitable for the treatment of aphthous ulcers and other conditions giving rise to pain and/or irritation in the oral cavity.

BRIEF SUMMARY

According to a first embodiment of the present invention there is provided an oral care composition comprising a local anaesthetic agent, a film-forming polymer and a non-aqueous vehicle wherein the film-forming polymer comprises an alkyl vinyl ether-maleic acid or anhydride copolymer or salt thereof.

Optionally the oral care composition comprises a local anaesthetic agent selected from benzocaine, procaine, tetracaine, pramocaine, dibucaine, lidocaine, prilocaine and mixtures thereof. Further optionally the composition comprises benzocaine.

Optionally the oral care composition comprises a methyl vinyl ether and maleic anhydride copolymer or salt thereof. Further optionally the composition comprises a mixed sodium and calcium salt of methyl vinyl ether and maleic anhydride copolymer.

Optionally the composition comprises a mixture of hydrocarbons. Further optionally the composition comprises a mixture of non-straight chain solid hydrocarbons and liquid hydrocarbons. Further optionally the composition comprises petrolatum.

Optionally the oral care composition comprises 0.5 weight % to 40 weight % local anaesthetic agent based on the total weight of the oral care composition. Further optionally the composition comprises 1.0 weight % to 35 weight % local anaesthetic agent based on the total weight of the oral care composition. Further optionally the composition comprises 5.0 weight % to 30 weight % local anaesthetic agent based on the total weight of the oral care composition. Further optionally the composition comprises 15 weight % to 25 weight % local anaesthetic agent based on the total weight of the oral care composition. Further optionally the composition comprises 18 weight % to 22 weight % local anaesthetic agent based on the total weight of the oral care composition.

Optionally the oral care composition comprises 0.1 weight % to 10.0 weight % film-forming polymer based on the total weight of the oral care composition. Further optionally the composition comprises 0.1 weight % to 5.0 weight % film-forming polymer based on the total weight of the oral care composition. Further optionally the composition comprises 0.5 weight % to 4.5 weight % film-forming polymer based on the total weight of the oral care composition. Further optionally the composition comprises 1.0 weight % to 4.0 weight % film-forming polymer based on the total weight of the oral care composition. Further optionally the composition comprises 2.0 weight % to 3.0 weight % film-forming polymer based on the total weight of the oral care composition.

Optionally the oral care composition comprises 2.0 weight % to 3.0 weight % based on the total weight of the oral care composition mixed sodium and calcium salt of methyl vinyl ether and maleic anhydride copolymer.

Optionally the oral care composition comprises 10 weight % to 75 weight % non-aqueous vehicle. Further optionally the composition comprises 25 weight % to 65 weight % non-aqueous vehicle. Further optionally the composition comprises 35 weight % to 55 weight % non-aqueous vehicle. Further optionally the composition comprises 40 weight % to 50 weight % non-aqueous vehicle. Further optionally the composition comprises 40 weight % to 50 weight % petrolatum.

Optionally the oral care composition further comprises mineral oil. Further optionally the composition comprises 0.1 to 20% mineral oil based on the total weight of the composition. Further optionally the composition comprises 1.0 to 20% mineral oil based on the total weight of the composition. Further optionally the composition comprises 2.5 to 15% mineral oil based on the total weight of the composition.

Optionally the oral care composition comprises 2.5 to 15% mineral oil, 0.1 weight % to 5.0 weight % film-forming polymer and 25 weight % to 65 weight % petrolatum, based on the total weight of the composition.

Optionally the composition comprises mineral oil, film-forming polymer and petrolatum in a weight ratio mineral oil:film-forming polymer:petrolatum of 1.5-5.0:1:15-20.

Optionally the oral care composition is in the form of a gel, cream, paste or strip.

Optionally the oral care composition comprises less than 5% water.

According to a further embodiment of the invention there is provided a method of alleviating pain or irritation in the oral cavity of a mammal comprising applying the oral care compositions described herein to a surface in the oral cavity.

According to a further embodiment of the invention there is provided a method of treating aphthous stomatitis comprising applying the oral care compositions of the invention to a surface in the oral cavity.

According to a further embodiment of the invention there is provided a method of local anesthesia comprising applying the oral care compositions of the invention to a surface in the oral cavity of a mammal.

According to a further embodiment of the invention there is provided the compositions as described herein for use in alleviating pain or irritation in the oral cavity of a mammal.

According to a further embodiment of the invention there is provided the compositions as described herein for use in treating aphthous stomatitis.

According to a further embodiment of the invention there is provided the compositions as described herein for use in local anesthesia of the oral cavity of a mammal.

According to a further embodiment of the invention there is provided use of an oral care composition as described herein to alleviate pain or irritation in the oral cavity of a mammal.

According to a further embodiment of the invention there is provided use of an oral care composition as described herein to treat aphthous stomatitis.

According to a further embodiment of the invention there is provided use of a composition as described herein to provide local anesthesia to the oral cavity of a mammal.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION

The following description of the preferred embodiment(s) is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

Topical local anaesthetic agents can be used to treat pain and irritation in the oral cavity, and in particular can be used to treat aphthous ulcers (also known as mouth ulcers or canker sores) and other mucocutaneous disorders. Topical local anaesthetic agents can also be used to provide relief from pain and irritation caused by minor injury to the mouth or gums, and pain and irritation resulting from the use of dentures or orthodontic appliances. It has surprisingly been discovered that formulating a composition comprising a local anaesthetic agent with a non-aqueous vehicle and a specific film-forming polymer can improve the retention of such a composition on oral cavity surfaces. Thus the compositions of the invention have been found to possess improved product adhesion. Furthermore, the compositions of the invention have surprisingly been found to provide increased duration of numbing, resulting in improved product efficacy.

Local anesthetics cause temporary local anesthesia and generally belong to two chemical classes: aminoamides and aminoesters. The compositions of the present invention comprise a toxicologically-acceptable local anaesthetic agent. In certain embodiments the compositions comprise at least one aminoamide or aminoester local anaesthetic agent. In certain embodiments the compositions may comprise a local anaesthetic selected from benzocaine, procaine, tetracaine, pramocaine, dibucaine, lidocaine, prilocaine and mixtures thereof. Benzocaine (ethyl ester of p-aminobenzoic acid) is particularly preferred.

In certain embodiments, the compositions comprise 0.5 weight % to 40 weight % local anaesthetic agent based on the total weight of the oral care composition. For example, the compositions of the invention may comprise 1.0 weight % to 35 weight % local anaesthetic agent, 5.0 weight % to 30 weight % local anaesthetic agent, 10 weight % to 30 weight % local anaesthetic agent, 15 weight % to 30 weight % local anaesthetic agent, 15 weight % to 25 weight % local anaesthetic agent or 18 weight % to 22 weight % local anaesthetic agent. In certain embodiments, the oral care compositions may comprise about 20 weight % local anaesthetic agent. In preferred embodiments, the compositions comprise 0.5 weight % to 40 weight % benzocaine based on the total weight of the oral care composition. For example, the compositions of the invention may comprise 1.0 weight % to 35 weight % benzocaine, 5.0 weight % to 30 weight % benzocaine, 10 weight % to 30 weight % benzocaine, 15 weight % to 30 weight % benzocaine, 15 weight % to 25 weight % benzocaine or 18 weight % to 22 weight % benzocaine. In certain embodiments, the oral care compositions may comprise about 20 weight % benzocaine.

The compositions of the present invention comprise a film-forming polymer which comprises an alkyl vinyl ether-maleic acid or anhydride copolymer or salt thereof. In particularly preferred embodiments, the compositions comprise a methyl vinyl ether and maleic anhydride copolymer or salt thereof, for example a mixed sodium and calcium salt of methyl vinyl ether and maleic anhydride copolymer. Such a polymer can provide a solution with high viscosity and adhesion as the cations form salt bridges crosslinking the polymer chains. In certain embodiments, the film-forming polymer has a molecular weight of 500,000 to 1,500,000 Daltons, for example around 1,000,000 Daltons. In certain embodiments the film-forming polymer has the chemical structure:

—[CH$_2$—CH(OCH$_3$)—CH(COONa)—CFHCOONa]$_n$—[CH$_2$—CHOCH$_3$—CH(COO$^-$)—CH(COO$^-$)Ca$^{2+}$]$_M$—

In certain embodiments the compositions comprise as film-forming polymer a calcium/sodium PVM/MA copolymer such as GANTREZ MS-955.

In certain embodiments the compositions may comprise 0.1 weight % to 10.0 weight % film-forming polymer based on the total weight of the oral care composition. For example the compositions may comprise 0.1 weight % to 5.0 weight %, 0.5 weight % to 5.0 weight %, 0.5 weight % to 4.5 weight %, 1.0 weight % to 4.0 weight % or 2.0 weight % to 3.0 weight % film-forming polymer based on the total weight of the oral care composition. In particularly preferred embodiments the compositions comprises about 2.5 weight % film-forming polymer based on the total weight of the oral care composition.

In certain embodiments the compositions comprise 0.1 weight % to 5.0 weight %, 0.5 weight % to 5.0 weight %, 0.5 weight % to 4.5 weight %, 1.0 weight % to 4.0 weight % or 2.0 weight % to 3.0 weight % mixed sodium and calcium salt of methyl vinyl ether and maleic anhydride copolymer, for example about 2.5 weight % mixed sodium and calcium salt of methyl vinyl ether and maleic anhydride copolymer.

The compositions of the present invention comprise a non-aqueous vehicle. In certain embodiments this vehicle may be a water-insoluble liquid, gel, thermoplastic solid or a combination thereof. The non-aqueous vehicle is typically substantially free of water. For example, the non-aqueous vehicle may comprise less than 5% by weight water, based on the total weight of the non-aqueous vehicle. In certain embodiments the non-aqueous vehicle may comprise less than 2% by weight, less than 1% by weight, less than 0.5% by weight, less than 0.1% by weight or less than 0.01% by weight water. In certain embodiments the non-aqueous vehicle may be entirely free of water. In certain embodiments the non-aqueous vehicle comprises or consists of a mixture of hydrocarbons. For example in certain embodiments the non-aqueous vehicle comprises or consists of a semi-solid hydrocarbon mixture such as petrolatum. Petrolatum (also known as petroleum jelly, paraffin jelly or VASELINE) is a colloidal system of nonstraight-chain solid hydrocarbons and high-boiling liquid hydrocarbons with a melting point of 38-54°. Petrolatum is derived from petroleum by distillation of paraffin-base petroleum fractions.

In certain embodiments the compositions comprise 10 weight % to 75 weight % non-aqueous vehicle, for example 25 weight % to 65 weight %, 35 weight % to 55 weight % or 40 weight % to 50 weight % non-aqueous vehicle based on the total weight of the oral care composition. In certain embodiments the compositions comprise 10 weight % to 75 weight % petrolatum, for example 25 weight % to 65 weight %, 35 weight % to 55 weight % or 40 weight % to 50 weight % petrolatum based on the total weight of the oral care composition.

In certain embodiments the compositions of the present invention also comprise a plasticizer such as a liquid oil. In certain preferred embodiments the compositions comprises mineral oil. The mineral oil may be white, light or technical. In certain embodiments the mineral oil has a specific gravity at 25° of 0.80 to 0.90 measured using ASTM D4062. For example, the mineral oil may be a HYDROBRITE® mineral oil such as HYDROBRITE® PVC White Mineral Oil, HYDROBRITE® HV White Mineral Oil, HYDROBRITE® 380 PO White Mineral Oil, HYDROBRITE® 380-EU White Mineral Oil, HYDROBRITE® 550 PO White Mineral Oil, HYDROBRITE® 200 PO White Mineral Oil or HYDROBRITE® 1000 PO White Mineral Oil.

In certain embodiments the compositions comprise 0.1 to 20 weight % mineral oil based on the total weight of the composition. For example the compositions may comprise 1.0 to 20 weight % mineral oil, 1.0 to 15 weight % mineral oil, 2.5 to 15 weight % mineral oil, 2.5 to 10 weight % or 5.0 to 10 weight % mineral oil mineral oil based on the total weight of the composition. In certain embodiments the compositions comprise about 7.5 weight % mineral oil based on the total weight of the composition.

In certain embodiments the compositions comprise 2.5 to 15% mineral oil, 0.1 weight % to 5.0 weight % film-forming polymer and 25 weight % to 65 weight % petrolatum, based on the total weight of the composition. In certain embodiments the compositions comprise 5.0 to 10 weight % mineral oil, 1.5 weight % to 4.0 weight % film-forming polymer and 40 weight % to 60 weight % petrolatum, based on the total weight of the composition.

In certain embodiments the compositions comprise both mineral oil and petrolatum. In certain embodiments the compositions comprise 45 to 60 weight % mineral oil and petrolatum based on the total weight of the composition. In certain embodiments the compositions comprise 50 to 60 weight %, 52 to 57 weight % or 53 to 55 weight % mineral oil and petrolatum based on the total weight of the composition.

In certain embodiments the compositions comprise (i) mineral oil, (ii) an alkyl vinyl ether-maleic acid or anhydride copolymer or salt thereof film-forming polymer and (iii) petrolatum in a weight ratio of 1.5-5.0:1:15-20.

The oral compositions of the present invention can be formulated as a gel, cream, paste or strip. In certain embodiments the compositions can comprise a water-insoluble blend of mineral oil and petrolatum which can be used to formulate the composition into a suspension of solid-particles in a liquid/gel vehicle or carrier.

In certain embodiments the compositions comprise less than 5 weight %, less than 3 weight % or less than 2 weight % water based on the total weight of the composition.

In certain embodiments the compositions further comprise a hydrocolloid, which may serve as an emulsifying, thickening and/or gelling agent. In certain embodiments for example, the compositions may comprise plant exudates such as gum Arabic, seaweed extracts such as xanthan gum, agar and carrageenan gum; plant seed gums or mucilages such as guar gum; cereal gums such as starches; fermentation gums such as dextran; animal products such as gelatin; or any combinations of any of these hydrocolloids. In certain embodiments the compositions may comprise from 2.5 weight % to 15 weight % hydrocolloid. A preferred hydrocolloid is xanthan gum. In certain embodiments, the compositions comprise from 2.5 weight % to 15 weight % xanthan gum based on the total weight of the composition, for example 5.0 weight % to 10 weight % xanthan gum or 6.0 weight % to 8.5 weight % xanthan gum.

In certain embodiments the compositions further comprise a heteropolysaccharide, such as a heteropolysaccharide derived from plant cell walls. In certain embodiments, the heteropolysaccharide may be esterified e.g. partially methyl esterified, and my serve as an emulsifying, thickening and/or gelling agent. A preferred heteropolysaccharide is pectin. In certain embodiments, the compositions comprise from 2.5 weight % to 15 weight % pectin based on the total weight of the composition, for example 5.0 weight % to 10 weight % pectin or 6.0 weight % to 8.5 weight % pectin.

In certain embodiments the compositions may comprise a cellulose derivative, for example carboxy methyl cellulose. In certain embodiments the compositions may comprises carboxy methyl cellulose in an amount of from 2.5 weight % to 15 weight % carboxy methyl cellulose based on the total weight of the composition, for example 5.0 weight % to 10 weight % carboxy methyl cellulose or 6.0 weight % to 8.5 weight % carboxy methyl cellulose.

In certain embodiments the compositions may comprise a combination of a carboxymethyl cellulose, xanthan gum and pectin. In certain embodiments the compositions may comprise 6.0 weight % to 8.5 weight % carboxy methyl cellulose, 6.0 weight % to 8.5 weight % pectin and 6.0 weight % to 8.5 weight % xanthan gum.

The compositions of the present invention provide excellent retentivity in the oral cavity and can be used to alleviate pain or irritation caused by aphthous stomatitis, dentures and orthodontic appliances. The compositions may be applied by hand or using an applicator such as a cotton swab. The compositions may be applied to the affected area several days per day, for example up to four times per day. In certain embodiments the compositions of the present invention may provide anesthesia and/or an analgesic effect, alleviate pain or alleviate irritation for a duration up to 24 hours, for example up to 12 hours, 8 hours, 6 hours, 4 hours, 3 hours, 2 hours or 1 hour after application.

EXAMPLES

Example 1

An in vitro model was used to test the retentivity of the compositions. A composition of the invention comprising petrolatum and approximately 2.5 weight % GANTREZ was compared to Comparative Formulation A comprising plastigel (a mixture of polyethylene and mineral oil) as a stabilizer, binder agent and film-forming agent and 20% benzocaine as a local anaesthetic, and Comparative Formulation B in which the plastigel is replaced with petrolatum. These formulations are shown in Table 1:

TABLE 1

| Component | Comparative Formulation A weight % | Comparative formulation B weight % | Formulation 1 weight % |
|---|---|---|---|
| Plastigel | 49.15 | 0 | 0 |
| Petrolatum | 0 | 49.15 | 52.28 |
| Benzocaine | 20.00 | 20.00 | 21.28 |
| Sodium carboxymethylcellulose | 9.95 | 9.95 | 7.57 |
| Xanthan gum | 9.95 | 9.95 | 7.57 |
| Pectin | 9.95 | 9.95 | 7.57 |
| Gantrez MS 955 | 0 | 0 | 2.66 |
| Flavor | 1.00 | 1.00 | 1.06 |

A 150 ml glass beaker was filled with 100 ml water and a stir bar added. A glass microscope slide was marked from 0.5" and 2" from one edge with black lines from an indelible marker. The slide was weighed and the surface between the black lines covered with 0.3 g test formula before smoothing with a flat spatula. The slide was then re-weighed. The slide was placed in the beaker with the formula coated surface face down into the water. The beaker was stirred strongly to induce a vortex and mixed for approximately 1 hour 45 minutes. The glass slides were then removed, re-weighed and the percentage weight lost calculated. The results are shown in Table 2:

TABLE 2

| Test Formula | % Weight Loss |
|---|---|
| Comparative Formulation A | 73.3 |
| Comparative Formulation B | 33.3 |
| Formulation 1 | 16.7 |

Example 2

Although possessing excellent retentivity, Formulation 1 was found to be more difficult to dispense than compositions comprising plastigel. In order to combine improved retentivity with good dispensing properties, compositions were formulated comprising mineral oil, GANTREZ and petrolatum as shown in Tables 3 and 4.

TABLE 3

| Component | Formulation 2 weight % | Formulation 3 weight % | Formulation 4 weight % |
|---|---|---|---|
| Plastigel | 0 | 0 | 0 |
| Mineral oil HYDROBRITE ® M28221 | 10 | 7.5 | 5.0 |
| Petrolatum | 44.15 | 46.65 | 49.15 |
| Benzocaine | 20.00 | 20.00 | 20.00 |
| Sodium carboxymethylcellulose | 7.45 | 7.45 | 7.45 |
| Xanthan gum | 7.45 | 7.45 | 7.45 |
| Pectin | 7.45 | 7.45 | 7.45 |
| Gantrez MS 955 | 2.5 | 2.5 | 2.5 |
| Flavor | 1.00 | 1.00 | 1.00 |

TABLE 4

| Component | Formulation 5 weight % | Formulation 6 weight % | Formulation 7 weight % |
|---|---|---|---|
| Plastigel | 0 | 0 | 0 |
| Mineral oil M32637 | 2.5 | 5 | 10.0 |
| Petrolatum | 49.15 | 49.15 | 44.15 |
| Benzocaine | 20.00 | 20.00 | 20.00 |
| Sodium carboxymethylcellulose | 8.29 | 7.45 | 7.45 |
| Xanthan gum | 8.28 | 7.45 | 7.45 |
| Pectin | 8.28 | 7.45 | 7.45 |
| Gantrez MS 955 | 2.5 | 2.5 | 2.5 |
| Flavor | 1.00 | 1.00 | 1.00 |

Retentivity experiments were carried out as described for Example 1 and the results are shown in Tables 5 and 6:

TABLE 5

| Test Formula | % Weight Loss |
|---|---|
| Comparative Formulation A | 68.89 |
| Formulation 2 | 11.11 |
| Formulation 3 | 11.11 |
| Formulation 4 | 6.67 |

TABLE 6

| Test Formula | % Weight Loss |
|---|---|
| Comparative Formulation A | 70.0 |
| Formulation 5 | 20.0 |
| Formulation 6 | 7.8 |
| Formulation 7 | 12.2 |

These formulations were found to possess improved retention relative to Comparative Formulation A and also to possess good dispensing properties.

Example 3

Consumer tests were run using formulations comprising 7.5% or 5.0% HYDROBRITE® mineral oil compared to Comparative Formulation A as a control. Consumers were asked to rate the formulations for numbing and duration of numbing. The results are shown in Tables 9 to 14:

Comparative Formulation A:

TABLE 9

| Numbing Ability of Formulation | % Consumers |
|---|---|
| Much too numbing | 17 |
| Just about right numbing | 50 |
| Not at all numbing | 33 |

5.0% HYDROBRITE® Mineral Oil Formulation:

TABLE 10

| Numbing Ability of Formulation | % Consumers |
|---|---|
| Much too numbing | 11 |
| Just about right numbing | 50 |
| Not at all numbing | 39 |

7.5% HYDROBRITE® Mineral Oil Formulation:

TABLE 11

| Numbing Ability of Formulation | % Consumers |
|---|---|
| Much too numbing | 17 |
| Just about right numbing | 56 |
| Not at all numbing | 28 |

Comparative Formulation A:

TABLE 12

| Duration of Numbing | % Consumers |
|---|---|
| Much longer than desired | 11 |
| Just about right duration | 44 |
| Much shorter than desired | 44 |

5.0% HYDROBRITE® Mineral Oil Formulation:

TABLE 13

| Duration of Numbing | % Consumers |
|---|---|
| Much longer than desired | 6 |
| Just about right duration | 44 |
| Much shorter than desired | 50 |

7.5% HYDROBRITE® mineral oil formulation:

TABLE 14

| Duration of Numbing | % Consumers |
|---|---|
| Much longer than desired | 0 |
| Just about right duration | 72 |
| Much shorter than desired | 28 |

These results show that the formulations of the invention lead to both improved product adhesion and improved product efficacy, especially by increasing the duration of numbing.

What is claimed is:

1. An oral care composition comprising a local anaesthetic agent, a film-forming polymer, 35 weight % to 55 weight % petrolatum and 2.5 weight % to 15 weight % mineral oil, wherein the film-forming polymer comprises a mixed sodium and calcium salt of methyl vinyl ether-maleic acid or anhydride copolymer in an amount of 1.0 weight % to 4.0 weight %.

2. The oral care composition of claim 1 wherein the composition comprises a local anaesthetic agent selected from benzocaine, procaine, tetracaine, pramocaine, dibucaine, lidocaine, prilocaine and mixtures thereof.

3. The oral care composition of claim 1, wherein the composition comprises benzocaine.

4. The oral care composition of claim 1, comprising 0.5 weight % to 40 weight % local anaesthetic agent based on the total weight of the oral care composition.

5. The oral care composition of claim 1, comprising 2.0 weight % to 3.0 weight % based on the total weight of the oral care composition mixed sodium and calcium salt of methyl vinyl ether and maleic anhydride copolymer.

6. The oral care composition of claim 1, comprising 40 weight % to 50 weight % petrolatum.

7. The oral care composition of claim 1, comprising 5.0 weight % to 10 weight % mineral oil based on the total weight of the composition.

8. The oral care composition of claim 1, wherein the composition comprises mineral oil, film-forming polymer and petrolatum in a weight ratio mineral oil:film-forming polymer:petrolatum of 1.5-5.0:1:15-20.

9. The oral care composition of claim 1, wherein the composition is in the form of a gel, cream, paste or strip.

10. The oral care composition of claim 1, wherein the composition comprises less than 5% water.

11. A method of (i) alleviating pain or irritation in the oral cavity of a mammal (ii) treating aphthous stomatitis and/or (iii) local anesthesia comprising applying the oral care composition of claim 1 to a surface in the oral cavity.

12. The oral care composition of claim 1 for use in (i) alleviating pain or irritation in the oral cavity of a mammal (ii) treating aphthous stomatitis and/or (iii) local anesthesia of the oral cavity of a mammal.

13. The oral care composition of claim 1, wherein the composition comprises 40 weight % to 50 weight % petrolatum and 5.0 weight % to 10 weight % mineral oil based on the total weight of the composition, wherein the film-forming polymer comprises a mixed sodium and calcium salt of methyl vinyl ether and maleic anhydride copolymer in an amount of 2.0 weight % to 3.0 weight % based on the total weight of the oral care composition.

* * * * *